(12) United States Patent
Gandy et al.

(10) Patent No.: US 6,528,693 B1
(45) Date of Patent: Mar. 4, 2003

(54) PREPARATION OF CYCLOPROPYLETHYNE AND INTERMEDIATES FOR PREPARATION OF CYCLOPROPYLETHYNE

(75) Inventors: Robert Gandy, Liverpool (GB); Peter John Cremins, Manchester (GB); Allan Williams Timms, Ellesmere Port (GB)

(73) Assignee: Great Lakes (UK) Limited, Cheshire (GB)

( * ) Notice: Subject to any disclaimer, the term of this patent is extended or adjusted under 35 U.S.C. 154(b) by 0 days.

(21) Appl. No.: 09/806,980

(22) PCT Filed: Oct. 12, 1998

(86) PCT No.: PCT/GB98/03043

§ 371 (c)(1),
(2), (4) Date: Apr. 5, 2001

(87) PCT Pub. No.: WO00/21912

PCT Pub. Date: Apr. 20, 2000

(51) Int. Cl.[7] ............... C07C 17/02; C07C 2/00
(52) U.S. Cl. ............... 570/217; 585/312; 585/317; 585/359
(58) Field of Search ............... 570/217; 585/317, 585/312, 359

(56) References Cited

U.S. PATENT DOCUMENTS 3,715,407 A    2/1973   Relles

FOREIGN PATENT DOCUMENTS

| GB | 2 329 384 | 3/1999 |
|----|-----------|--------|
| WO | WO9840333 | 9/1998 |
| WO | WO 98/40333 | 9/1998 |

OTHER PUBLICATIONS

Chemical Abstracts 87:200900 (1977), abstracting Soviet Union Patent 555079, issued Apr. 25, 1977.
Chemical Abstracts 88:89193 (1978), abstracting Soviet Union Patent 572445, issued Sep. 15, 1977.
Chemical Abstracts 88:89194 (1978), abstracting Soviet Union Patent 578293, issued Oct. 30, 1977.

*Primary Examiner*—Alan Siegel
(74) *Attorney, Agent, or Firm*—Drinker Biddle & Reath LLP

(57) ABSTRACT

1-chloropropylethyne is prepared by dehydrochlorination with a base of 1-chloro-1-cyclopropylethene, which is itself prepared by treating 1-cyclopropylethanone with dichlorotriarylphosphorane or dichlorotrialkylphosphorane in the presence of a base.

28 Claims, No Drawings

PREPARATION OF CYCLOPROPYLETHYNE AND INTERMEDIATES FOR PREPARATION OF CYCLOPROPYLETHYNE

This application is a 371 of PCT/GB98/03043 filed Oct. 12, 1998.

DESCRIPTION

This invention concerns a process for preparing cyclopropylethyne as well as a process for preparing intermediates for making cyclopropylethyne.

Cyclopropylethyne is used, for example, as an intermediate in the synthesis of the important HIV reverse transcriptase inhibitor of the following structure:

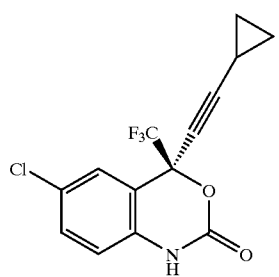

There are two main syntheses for cyclopropylethyne already disclosed in the literature. These are:

1. Chlorination of cyclopropyl methyl ketone with phosphorus pentachloride to give 1,1-dichloro-1-cyclopropylethane followed by dehydrochlorination with a strong base

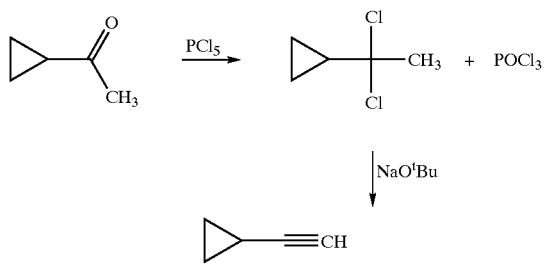

2. Reaction of 5-chloro-1-pentyne with 2 equivalents of butyl lithium to effect cyclisation.

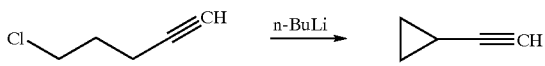

Whilst these methods work well on a laboratory scale, manufacture on a production scale is difficult. The intermediate, 1,1-dichloro-1-cyclopropylethane produced in the first literature route is a very labile molecule and is thermally and hydrolytically unstable. For example, whilst chlorination of cyclopropyl methyl ketone with phosphorus pentachloride proceeds quite well even on a large scale, the isolation of the 1,1-dichloro-1-cyclopropylethane from the reaction mixture (which necessarily contains phosphorus oxychloride) can lead to extensive decomposition of the product. The phosphorus oxychloride may be removed by decomposition with water. Such a process is very exothermic and unless the reaction mixture is kept cool the product is decomposed by both aqueous acids and alkalis. The cooling requirements on a plant scale would be enormous. This leads to a very high capital investment in plant. If the feed time is extended to overcome the deficiencies in the cooling systems, decomposition also occurs and leads to very low yields of the target compound.

It is also possible to remove the phosphorus oxychloride by fractional distillation. However, in a conventional pot still, extensive decomposition due to ring opening can occur resulting in low yields.

Once the required 1,1-dichloro-1-cyclopropylethane has been obtained in a pure form, dehydrochlorination to give the required compound can also lead to problems. As stated above, the compound is both thermally unstable and also unstable to alkalis. Thus to effect dehyrochlorination, a hindered base in a dipolar aprotic solvent is required so that elimination rather than substitution is the major synthetic pathway. Because of the stoichiometry of the process at least two equivalents of expensive base are required. This seriously increases the cost of manufacture.

The method of manufacture where 5-chloro-1-pentyne is ring closed by means of at least 2 equivalents of n-butyl lithium also works quite well in the laboratory. However, the cost of n-butyl lithium makes manufacture by this route an expensive option. Furthermore, specialised plant is required to handle the pyrophoric concentrated solutions that an efficient synthesis dictates.

WO98/40333A (BASF Aktiengesellschaft) discloses a process for halogenating cyclopropylmethyl ketone with at least one dihalogen triorganophosphorane as well as a process for converting the halogenated cyclopropyl methyl ketone into cyclopropylacetylene.

A first object of this invention is to provide a process for preparing an intermediate for preparation of cyclopropylethyne, which is both thermally and hydrolytically stable and does not involve use of expensive pyrophoric reagents.

A second object of this invention is to provide an improved process for preparing cyclopropylethyne.

It has been surprisingly found that a suitable intermediate for use in preparing cyclopropylethyne is 1-chloro-1-cyclopropylethene.

According to a first aspect of this invention there is provided a process for preparing 1-chloro-1-cyclopropylethene comprising treating 1-cyclopropylethanone with dichlorotriaryl phosphorane or dichlorotriakyl phosphorane in the presence of a base in an inert solvent characterised in that the base is a tertiary amine.

According to a second aspect of this invention there is provided a process for preparing cyclopropylethyne comprising the steps of preparing 1-chloro-1-cyclopropylethene by chlorinating 1-cyclopropylethanone with dichlorotriarylphosphorane or dichlorotriakylphosphorane in the presence of a base in an inert solvent and dehydrochlorinating the 1-chloro-1-cyclopropylethene with a strong base in an inert solvent, characterised in that the base in the chlorination stage is a tertiary amine.

The 1-chloro-1-cyclopropylethene used in the process of the second aspect of the invention may be that prepared by the process of the first aspect of the invention.

A benefit of using 1-chloro-1-cyclopropylethene is that, in principle, only one equivalent of strong base is required to bring about the dehydrochlorination. Furthermore, this base does not need to be an expensive alkali metal salt of a hindered tertiary alcohol. Simple hydroxides of alkali metals will suffice to bring about the transformation. The literature indicates that this intermediate may be prepared in reasonable yield by the mono-dehydrochlorination of 1,1-dichloro- 1-cyclopropylethane; an intermediate which has already been stated to be difficult to manufacture on a large scale. A better synthesis of 1-chloro-1-cyclopropylethene was therefore sought.

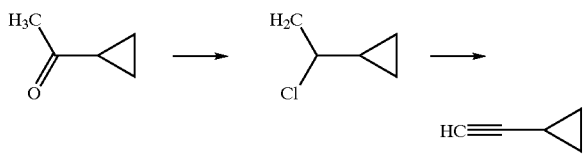

It is known that acetyl ketones will react with dichlorotriphenylphosphorane to afford the corresponding gem dichlorides. (U.S. Pat. No. 3,715,407). The reaction in the case of cyclopropyl methyl ketone has the complication that the cyclopropane ring is ruptured during the course of the reaction with the formation of compounds which were identified as dichloropentenes. It was considered that these by-products were formed by adventitious hydrogen chloride in the reaction mixture and that the inclusion of an organic base would prevent this side reaction occuring. When this experiment was carried out, the amount of ring opened dichloropentenes was greatly reduced from an experiment which did not contain base. We were surprised to find that only minor amounts of 1,1-dichloro-1-cyclopropylethane were formed but that 1-chloro-1-cyclopropylethene was formed in good yield. Furthermore, the amount of ring opened dichloropentenes were greatly reduced from an experiment which did not contain base. A convenient synthesis of the desired intermediate was thus opened to us.

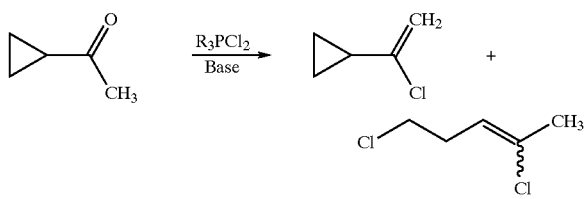

wherein R is an aryl group or an alkyl group.

The dichlorothiarysphohranes or the dichlorotrialkylphosphoranes may be prepared by reaction of the appropriate triarylphosphine or triarylphosphine oxide or trialkylphosphine or trialkylphosphine oxide with a chlorinating agent such as chlorine or phosgene. The chlorination stage may be carried out catalytically in situ particularly if phosgene is used. 1–100 mol % of trisubstituted phosphine or its oxide may be used. Less than 25 mol % of triarylphosphine or its oxide or trialkylphosphine or its oxide may be sufficient to bring about the transformation with 1–10 mol %, more preferably about 6 mol %, being close to the optimum in terms of yield and reaction velocity.

The organic base that is required for good reaction can be any base which does not react with phosgene or dichlorotriarylphosphorane or dichlorotrialkylphosphorane. In practice this means that tertiary amines are probably most suitable as the organic base. Pyridine and quinoline are particularly suitable since they appear to be inert to the phosgenation reaction conditions. Other tertiary amines such as triethylamine which may be used are less suitable since they can preferentially react with phosgene under the reaction conditions to give carcinogenic carbamoyl chlorides such as diethyl carbamoyl chloride. The production of even minor amounts of such carcinogens precludes the use of such tertiary amines in large scale manufacture.

As already described the thermal and hydrolytic stability of 1-chloro-1-cyclopropylethene is much greater than 1,1-dichloro-1-cyclopropylethane. This means that the work-up of the product is much simpler. The product may be distilled directly from the reaction mixture or quenched on to aqueous alkali and then phase separated from the aqueous layer and the organic phase fractionated. Due to formation of molar quantities of amine hydrochloride, it is necessary to use a solvent to provide mobility for the reaction. Almost any solvent which does not react under the reaction conditions may be used but it is most convenient to use one of sufficiently different boiling point which does not interfere with the distillation of the product, 1-chloro-1-cyclopropylethene, from the reaction mixture. Aromatic solvents, especially high boiling aromatic solvents are particularly useful since the reactants are soluble in these solvents and the distillation of the product from them is easy. 1,2-Dichlorobenzene is particularly usefull as a solvent.

The reaction is conveniently carried out in a temperature range of ambient, say, around 20° C., to about 100° C. At lower temperatures the reaction rate is such that the synthesis cannot be carried out in a reasonable time. At higher temperatures by-products begin to be formed with the concomitant reduction in yield. The optimum temperature in terms of reaction rate and specificity appears to be between 40° C. and 90° C., more preferably 70° C. to 80° C.

Dehydrochlorination of 1-chloro-1-cyclopropylethene can be effected with strong bases in a suitable solvent, for example any alcohol. Such strong bases are the alkali metal salts of hindered tertiary alcohols, alkali or alkaline earth hydroxides or the "super-bases". Examples of these bases are sodium or potassium $^t$butoxide, sodium or potassium hydroxide or 2,3,4,6,7,8,9,10-octahydropyrimido[1,2-a] azepine. Particularly useful are the alkali metal hydroxides with sodium hydroxide being very advantageous.

The solvent for the dehydrochlorination can be almost any solvent which does not react under the basic, hydrolytic conditions. Dipolar protic or aprotic solvents such as dimethyl sulphoxide are useful as solvent as are high boiling alcohols such as ethylene glycol. The temperature is not critical to the outcome of the reaction. The temperature is preferably in the range of ambient temperature to 100° C., preferably 55° C. to 65° C. Temperatures of about 60° C. appear to be satisfactory in terms of reaction rate. At the end of the reaction time, the product, cyclopropylacetylene, is isolated by simple ionation from the reaction mixture.

This invention will now be further described by means of the following Examples

EXAMPLE 1

Preparation of 1-chloro-1-cyclopropylethene

Gaseous phosgene (480 g, 4.85 mol) was passed into a sired solution of cyclopropyl methyl ketone (336 g, 4.0 mol), triphenylphosphine oxide (68 g, 0.25 mol) and quinoline (774 g, 6.0 mol) in 1,2-dichlorobenzene (280 cm$^3$) over a period of 6 to 7 hours at 70° C. to 80° C. An exothermic reaction occurred, carbon dioxide gas was evolved, and the reaction mixture gradually darkened to form a very dark mobile slurry. On completion of phosgene addition, the reaction mixture was warmed to 90° C. and then stirred at 90° C. to 100° C. for a further 5 hours to complete the reaction. The mixture was then cooled to 75° C. and the product, 1-chloro-1-cyclopropylethene removed by flash distillation by applying a vacuum of about 80 mm Hg.

The distillate, containing small amounts of dichloropentenes, 1,2-dichlorobenzene and quinoline was fractionated through a short fractionating column. 1-Chloro-1-cyclopropylethene (223 g, 54.7%) was obtained in >97% assay of bp 95° C. to 99° C.

EXAMPLE 2

Preparation of cyclopropylethyne 1-chloro-1-cyclopropylethene prepared in accordance with Example 1 (102 g, 1.0 mol) was fed into a stirred slurry of sodium hydroxide (80 g, 2.0 mol) in dimethyl sulphoxide (255 cm$^3$) containing a little water at 60° C. On completion of the addition, the reaction mixture was stirred for a further 10 hours at 60° C. to ensure complete reaction. On completion of the reaction the product was removed by distillation at atmospheric pressure, bp 57° C. to 62° C. The yield was 59.4 g (87.3%) with a purity of >98%.

What is claimed is:

1. A process for preparation of 1-chloro-1-cyclopropylethene comprising treating 1-cyclopropylethanone with dichlorotriarylphosphorane or dichlorotrialkylphosphorane in the presence of a base comprising a tertiary amine in an inert solvent, wherein the dichlorotriarylphosphorane is formed in situ by reaction of a triarylphosphine or triarylphosphine oxide with phosgene, and the dichlorotrialkylphosphorane is formed in situ by reaction of a trialkylphosphine or trialkylphosphine oxide with phosgene.

2. A process as claimed in claim 1, wherein the base is pyridine or quinoline.

3. A process as claimed in claim 1, wherein the solvent is an aromatic solvent.

4. A process as claimed in claim 3, wherein the solvent is 1,2-dichlorobenzene.

5. A process as claimed in claim 1, wherein the reaction is carried out between ambient temperature and 100° C.

6. A process as claimed in claim 5, wherein the reaction temperature is 70° C. to 80° C.

7. A process as claimed in claim 1, wherein the dichlorotriaryphosphorane is dichlorotriphenylphosphorane.

8. A process as claimed in claim 1 wherein 1–100 mol % of tri-substituted phosphine or its oxide is used.

9. A process as claimed in claim 8, wherein 1–10 mol % of tri-substituted phosphine or its oxide is used.

10. A process as claimed in claim 1 further comprising the step of dehydrochlorinating the 1-chloro-1-cyclopropylethene with a strong base in an inert solvent to form cyclopropylethyne.

11. A process for preparing cyclopropylethyne comprising the steps of preparing 1-chloro-1-cyclopropylethene by chlorinating dichlorotriarylphosphorane or dichlorotrialkylphosphorane in the presence of a base comprising a tertiary amine in an inert solvent and dehydrochlorinating the 1-chloro-1-cyclopropylethene with a strong base in an inert solvent, wherein the dichlorotriarylphosphorane is formed in situ by reaction of a triarylphosphine or triarylphosphine oxide with phosgene, and the dichlorotrialkylphosphorane is formed in situ by reaction of a trialkylphosphine or trialkylphosphine oxide with phosgene.

12. A process as claimed in claim 11, where the base in the chlorination stage is pyridine or quinoline.

13. A process as claimed in claim 11, wherein the solvent in the chlorination stage is an aromatic solvent.

14. A process as claimed in claim 13, wherein the solvent is 1,2-dichlorobenzene.

15. A process as claimed in claim 11, wherein the temperature of the chlorination stage is in the range of ambient temperature to 100° C.

16. A process as claimed in claim 15, wherein the reaction temperature is 70° C. to 80° C.

17. A process as claimed in claim 11, wherein the dichlorotriarylphosphorane is dichlorotriphenylphosphorane.

18. A process as claimed in claim 11 wherein 1–100 mol % of tri-substituted phosphine or its oxide is used.

19. A process as claimed in claim 18, wherein 1–10 mol % of tri-substituted phospine or its oxide is used.

20. A process as claimed in claim 11, wherein the base in the dehydrochlorination stage is an alkali metal or alkaline earth hydroxide.

21. A process as claimed in claim 11, wherein the base in the dehydrochlorination stage is an alkali metal salt of an alcohol.

22. A process as claimed in claim 20, wherein the base in the dehydrochlorination stage is sodium hydroxide.

23. A process as claimed in claim 21, wherein the base in the dehydrochlorination stage is sodium $^t$-butoxide.

24. A process as claimed in claim 11, wherein the dehydrochlorination stage is carried out in a dipolar protic or aprotic solvent.

25. A process as claimed in claim 24, wherein the solvent is dimethyl sulphoxide.

26. A process as claimed in claim 24, wherein the solvent is ethylene glycol.

27. A process as claimed in claim 11, wherein the temperature of the dehydrochlorination stage is in the range of ambient temperature to 100° C.

28. A process as claimed in claim 27, wherein the temperature of the dehydrochlorination stage is in the range 55° C. to 65° C.

* * * * *